United States Patent [19]
de la Caffiniere

[11] Patent Number: 5,531,748
[45] Date of Patent: Jul. 2, 1996

[54] OSTEOSYNTHESIS DEVICE FOR TROCHANTERIC OR TROCHANTERIC-DIAPHYSEAL FRACTURE

[75] Inventor: Jean-Yves de la Caffiniere, Paris, France

[73] Assignee: Fixano, Bourg En Breese, France

[21] Appl. No.: 245,239

[22] Filed: May 17, 1994

[51] Int. Cl.⁶ .................................................. A61B 17/76
[52] U.S. Cl. ....................................... 606/62; 606/65
[58] Field of Search ........................... 606/65, 66, 67, 606/68, 62, 64, 63, 73, 72, 61, 60, 59, 54, 98, 96, 99, 100, 104; 623/22, 23

[56] References Cited

U.S. PATENT DOCUMENTS

| | | | |
|---|---|---|---|
| 2,381,050 | 8/1945 | Hardinge | 606/65 X |
| 2,834,342 | 5/1958 | Yost | 606/67 |
| 3,530,854 | 9/1970 | Kearney | 606/67 X |
| 4,622,959 | 11/1986 | Marcus | 606/64 X |
| 4,827,917 | 5/1989 | Brumfield | |
| 5,032,125 | 7/1991 | Durham et al. | 606/62 |
| 5,122,141 | 6/1992 | Simpson et al. | 606/62 |
| 5,336,223 | 8/1994 | Rogers | 606/61 |

FOREIGN PATENT DOCUMENTS 0441577 2/1991 European Pat. Off. .
9206580 9/1992 Germany .

*Primary Examiner*—Stephan C. Pellegrino
*Assistant Examiner*—Guy V. Tucker
*Attorney, Agent, or Firm*—Oliff & Berridge

[57] ABSTRACT

The device includes a medullary rod that is locked to a bone of a patient and that has at least one threaded hole with an axis parallel to the femoral neck of the bone, at least one self-drilling, self-tapping screw designed to pass through the hole in the rod and to engage the femoral neck of the bone, at least one sleeve designed to fit around a proximal end of the screw and to be threaded into the hole in the rod, and a shoulder on the sleeve for immobilizing the sleeve relative to the rod. According to the invention, the proximal end of the screw has a circular cross section which is formed to slide within a bore in the sleeve. Each sleeve has a threaded exterior portion which engages the threaded hole, and a proximal end portion shaped to allow the sleeve to be threaded into the hole in the rod. The shoulder on the sleeve bears against the rod to immobilize the sleeve relative to the rod when the sleeve has been fully threaded into the hole.

6 Claims, 1 Drawing Sheet

OSTEOSYNTHESIS DEVICE FOR TROCHANTERIC OR TROCHANTERIC-DIAPHYSEAL FRACTURE

BACKGROUND OF THE INVENTION

The present invention relates to an osteosynthesis device for a trochanteric or trochanteric-diaphyseal fracture.

Reduction of such a fracture and holding the parts of the fractured bone for the time taken for the bone to consolidate requires insertion of at least one screw inside the femoral neck, said screw being supported both in the femoral head and in the cortex of the bone.

For this specific type of fracture, repair of which requires firm diaphyseal support, U.S. Pat. No. 4,827,917 teaches the use of a medullary rod which is locked at its distal part and which at its proximal part has at least one hole provided along an axis essentially parallel to the axis of the femoral neck, the aforesaid screw being designed to pass through this hole and be immobilized relative to the rod.

Preferably, self-drilling, self-tapping screws are used, which screws have a threaded distal end with a diameter larger than that of the shaft. In this case, as shown in European Patent Application No. 0 441 577 or German Utility Model No. 92 06 580, the aforesaid hole is provided in the rod having the diameter of the threaded distal end of the screw and, after the latter has been set in place, a sleeve is fitted onto the proximal end of the screw and through the hole in the rod to fill the space between the shaft of the screw and the rod.

The rod, generally tubular, is tapped at its proximal end, allowing installation of an adjusting screw which immobilizes the screw engaged in the bone or the sleeve engaged on the screw, relative to the rod.

This means of immobilization has the drawback of being complex in use, since it is necessary to screw in and tighten this adjusting screw at the proximal end of the rod while keeping the rod and screw in their proper relative positions.

Moreover, in view of the angle formed by the screw and the rod, the bearing surface of the end of the adjusting screw against the screw engaged in the bone or the aforesaid sleeve is limited, so that the possibility of play between the rod and the screw or the sleeve may occur over time, under the effect of repeated forces applied to this precise spot on the bone. A large tightening torque is necessary to minimize this risk of play, which contributes to making the installation of these devices complex.

Finally, such an adjusting screw makes the manufacture of these devices complex.

Moreover, in the prior devices, the screw or screws is/are immobilized rigidly relative to the rod. This rigid assembly proves to be undesirable for full consolidation of the bone since the positioning of the parts of the fractured bone may evolve in the course of bone consolidation. In certain extreme cases, the distal ends of the screws engaged in the bone may have traversed the femoral head in the course of bone consolidation.

The goal of the invention is to overcome these drawbacks.

SUMMARY OF THE INVENTION

The device to which it applies is of the aforesaid type comprising a medullary rod which is locked to the bone at the distal part and which comprises, at the proximal part, at least one hole provided along an axis substantially parallel to the axis of the femoral head, at least one self-drilling, self-tapping screw designed to be engaged in the bone through the hole, at least one sleeve designed to be fitted, after placement of the screw, onto the proximal end of the screw and through the hole in the rod, to fill the space between the shaft of the screw and the rod, and means for immobilizing the sleeve relative to the rod.

According to the invention, the shaft or shafts of the screw or screws has or have a circular cross section or circular cross sections, the hole or holes in the rod is or are tapped, and each sleeve has a thread that projects from its outer wall, which thread matches the hole or holes tapped in the rod, whereby a shoulder on the proximal side bears against the rod when the sleeve has been fully screwed into the hole, with a shaped proximal end to allow screwing the sleeve through the hole in the rod.

After installing the rod and the screw, the sleeve is joined to the rod by screwing and tightening. This screwing and tightening take place through the same hole as the hole through which the screws were introduced into the bone.

It is thus no longer necessary, as in the prior art, to install an adjusting screw, nor to maintain the screw and the sleeve in their proper relative positions, as long as this adjusting screw is tight.

In addition, immobilization of the sleeve relative to the rod is far more reliable over time than with the devices of the prior art, and manufacture of the device is considerably simplified.

Advantageously, the sleeve has a length such that its bore emerges at the outside of the bone after placement of the sleeve on the rod, and this bore is such that it allows the screw to slide relative to the sleeve.

The position of the screw relative to the rod can thus change and adapt to changes in the positions of the parts of the bone during bone consolidation.

Advantageously, the sleeve has an extension on the distal side in order to extend beyond the rod after placement, thus ensuring perfect axial guidance of the screw as it slides and eliminating any risk of it flexing under the effect of the vertical forces applied to the bone.

For its proper understanding, the invention will be described once more below with reference to the schematic drawings attached which represent, as a nonlimiting example, a preferred embodiment of the osteosynthesis device for a trochanteric or trochanteric-diaphyseal fracture to which it relates.

DESCRIPTION OF PREFERRED EMBODIMENTS

Figure 1:
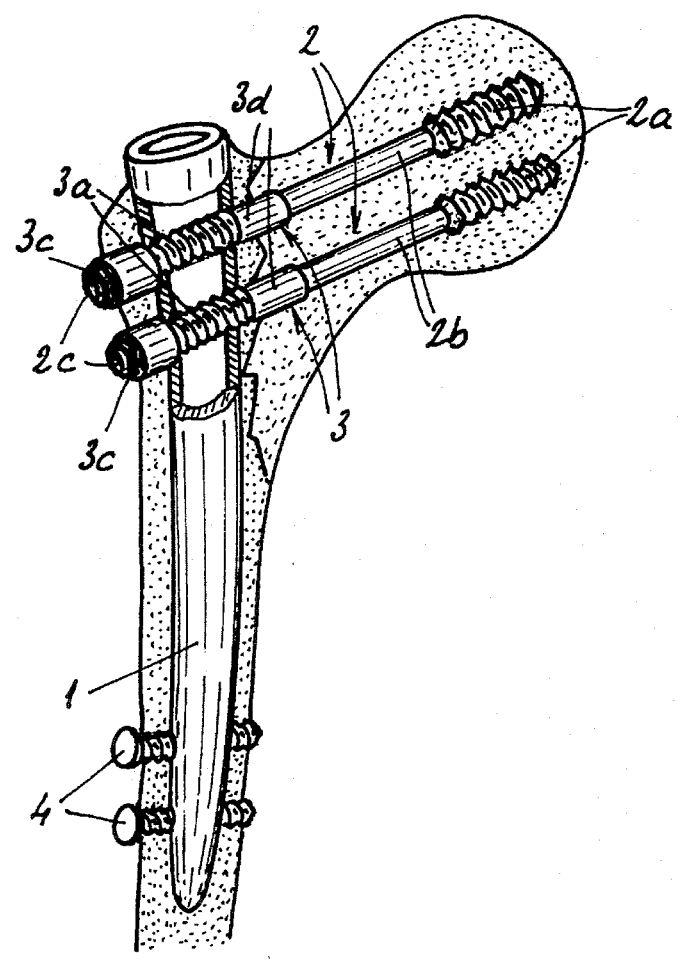
FIG. 1 is a perspective view in lengthwise section after fixation in a bone.

FIG. 1 represents an osteosynthesis device for trochanteric or trochanteric-diaphyseal fracture.

This device comprises a medullary rod 1, two self-drilling, self-tapping screws 2 and two sleeves 3.

Rod 1 is designed to be locked to the bone at the distal part by two cross screws 4 and comprises, at the proximal part, two tapped holes provided along an axis substantially parallel to the axis of the femoral neck, for passage of screws 2.

The latter have a circular cross section and have threaded distal ends 2a whose diameters are greater than that of their shafts 2b. The aforesaid tapped holes in Rod 1 are matched to the outside diameters of these ends 2a to allow the latter to pass through the former.

After rod 1 has been installed in the medullary cavity of the bone, screws 2 are in turn driven into the bone until their distal parts abut the femoral head. The two sleeves 3 are then fitted onto the proximal ends 2c of screws 2 to fill the gap between shafts 2b of screws 2 and rod 1.

Figure 2:
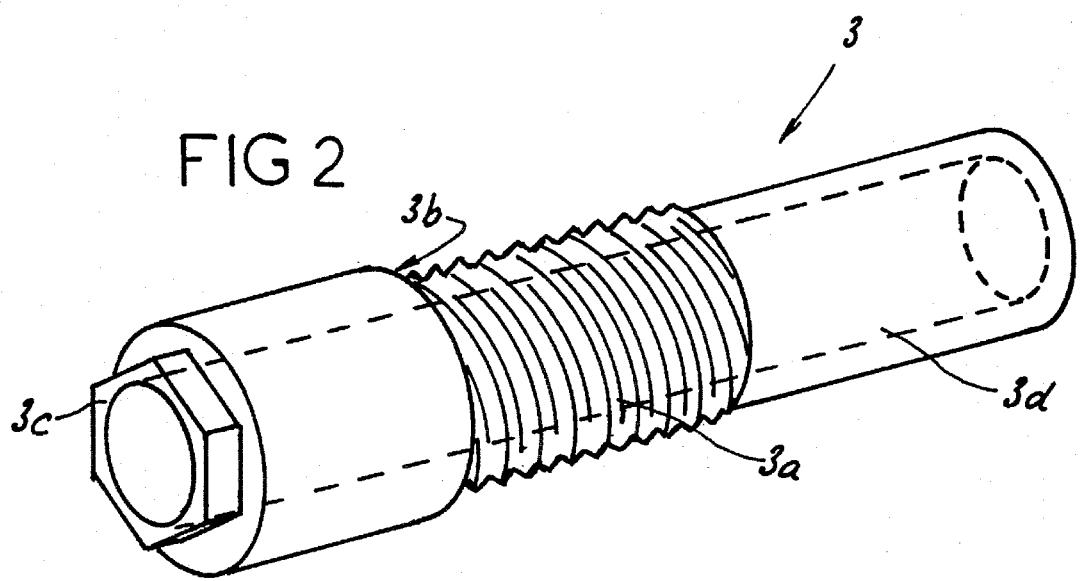
FIG. 2 is a perspective view on an enlarged scale of an element of which it is composed.

FIG. 2 shows one of these two sleeves 3 in greater detail.

It comprises:

a median thread 3a projecting from its outer wall, which thread 3a matches the holes tapped in rod 1;

a shoulder 3b at the proximal end, designed to bear against rod 1 when sleeve 3 has been screwed into the tapped hole;

a proximal end 3c with a hexagonal shape to allow sleeve 3 to be screwed through the hole in rod 1; and an extension 3d on the distal side.

In addition, sleeve 3 has a length such that its bore emerges at the outside of the bone after the sleeve has been installed, as shown in FIG. 1, and this bore is such as to allow screw 2 to slide relative to sleeve 3.

Thus, according to the invention, sleeves 3 are assembled to rod 1 by screwing and tightening after rod 1 and screws 2 have been fitted into the bone. This screwing and tightening are effected through the same holes as those that allowed screws 2 to be inserted into the bone.

Immobilization of sleeves 3 relative to rod 1 is extremely reliable over time and fully withstands the repeated forces applied to this precise point on the bone. There is no possibility of play between rod 1 and 2 sleeves 3.

Moreover, because the bores of sleeves 3 lead to the outside and these bores allow screws 2 to slide relative to sleeves 3, the positions of screws 2 relative to rod 1 can change over time and adapt to changes in position of the bone parts during bone consolidation.

Such dynamic osteosynthesis allows perfect consolidation to take place.

In addition, as appears in FIG. 1, the extensions 3d of sleeves 3 project beyond the rod 1 after installation, ensuring perfect axial sliding guidance of screws 2 and avoiding any risk of their flexing under the vertical forces exerted on the bone or the changes in relative position of the parts of the fractured bone during consolidation.

It goes without saying that the invention is not confined to the preferred embodiment described above but on the contrary covers all alternative embodiments.

Thus, it would not be a departure from the invention to provide only one screw 2, and hence only one sleeve 3.

What is claimed is:

1. An osteosynthesis device for a trochanteric or trochanteric-diaphyseal fracture, comprising:

a rod having at least one threaded hole at a proximal portion;

at least one screw passable through the at least one hole and having a distal portion engageable with a bone; and at least one cylindrical sleeve comprising:

a bore fittable around a proximal portion of the at least one screw;

a threaded intermediate exterior portion threadably engageable with the at least one hole;

a shoulder on a proximal exterior portion engageable with the rod for immobilizing the sleeve with respect to the rod when the sleeve is threaded into the at least one hole; and means for threading the sleeve into the at least one hole formed at a proximal end portion.

2. The osteosynthesis device of claim 1, wherein the means for threading the at least one sleeve into the at least one hole comprises one of hexagonal and octagonal head portions.

3. The osteosynthesis device of claim 1, wherein the rod is a medullary rod, a distal portion of the rod is fixable to a bone, the at least one hole has an axis adapted to be substantially parallel to a femoral neck of the bone; and wherein the at least one screw is inserted through the at least one hole, and the distal portion of the at least one screw is engageable with the femoral neck of the bone.

4. The osteosynthesis device of claim 3, wherein a proximal portion of the bore extends beyond the bone when the at least one sleeve is threaded into the at least one hole and is fixed to the rod such that the proximal portion of the at least one screw is slidable in the bore in an axial direction thereof.

5. The osteosynthesis device of claim 4, wherein a distal portion of the bore extends beyond the rod when the at least one sleeve is threaded into the at least one hole so as to fix the at least one sleeve to the rod such that the at least one screw is prevented from flexing in response to forces applied to the bone.

6. The osteosynthesis device of claim 3, wherein a distal portion of the bore extends beyond the rod when the at least one sleeve is threaded into the at least one hole so as to fix the at least one sleeve to the rod such that the at least one screw is prevented from flexing in response to forces applied to the bone.

* * * * *